United States Patent [19]

Bryan

[11] 4,318,163

[45] Mar. 2, 1982

[54] PROTECTIVE SHIELD FOR ULTRAVIOLET LAMPS

[76] Inventor: Emanuel Bryan, 2743 Rossiter Ave., Roslyn, Pa. 19001

[21] Appl. No.: 220,655

[22] Filed: Dec. 29, 1980

[51] Int. Cl.³ .............................................. F21V 11/00
[52] U.S. Cl. .................................... 362/359; 362/217; 362/303
[58] Field of Search ............... 362/277, 303, 313, 321, 362/359

[56] References Cited

U.S. PATENT DOCUMENTS

| | | | |
|---|---|---|---|
| 1,609,870 | 12/1926 | Ferree | 362/303 X |
| 3,922,031 | 11/1975 | Hugon | 362/359 X |
| 4,048,537 | 9/1977 | Blaisdell et al. | 362/217 X |
| 4,245,282 | 1/1981 | Sokol | 362/217 X |
| 4,247,884 | 1/1981 | McJunkin, Jr. | 362/217 X |

Primary Examiner—Peter A. Nelson
Attorney, Agent, or Firm—Caesar, Rivise, Bernstein & Cohen, Ltd.

[57] ABSTRACT

A protective shield for ultraviolet emiting fluorescent tubes including a pair of end caps through which electrical contacts extend. The shield is formed of a flexible plastic material which is transmissive to electromagnetic radiation in the ultraviolet spectrum and comprises a sleeve of a flexible film having a pair of open ends. Each of the ends includes an opposed pair of flaps including at least one opening therein. The sleeve is adapted to receive the fluorescent tube therein with the flaps at each end being folded over each other to overlap and cover an associated end cap of the fluorescent tube, and with the contacts of the tube extending through the openings in said flaps.

10 Claims, 4 Drawing Figures

PROTECTIVE SHIELD FOR ULTRAVIOLET LAMPS

This invention relates generally to protective shields for lamps and more particularly for shields for protecting fluorescent tubes.

In the interest of safety and pursuant to various federal, state and local regulations, fluorescent lamps are normally provided with a protective shield over the tubes to protect persons from injury in the event of tube breakage. In particular, fluorescent fixtures commonly include a transluscent or transparent cover panel or sheet disposed over the tubes in the fixture. In fixtures where the tubes would be exposed, that is where there is no cover sheet or panel, the fluorescent tubes are frequently disposed within transparent rigid plastic sleeves and are sealed therein by a respective pair of rigid end caps.

Artificial suntanning salons frequently utilize ultraviolet emitting fluorescent tubes for producing suntan in patients or clients. A common practice in such salons is to mount the ultraviolet emitting fluorescent tubes in uncovered fixtures on highly reflective walls of the booth or enclosure. While such an arrangement is effective for producing a suntan on persons within the enclosure, the close proximity of the exposed tubes presents a substantial hazard in the event of tube breakage.

Prior art shields, be they panels to cover a tube in a fixture or rigid sleeves enclosing otherwise exposed tubes, have not proved entirely suitable for suntan salon applications as well as various other applications involving ultraviolet emitting fluorescent tubes. In this regard, the relatively rigid tubular shields of the prior art frequently block or impede the transmission of ultraviolet radiation. Those rigid sleeve tubular shields which do at least initially permit the transmission of ultraviolet radiation therethrough frequently exhibit a tendency to degrade or discolor rapidly, so that they soon impede or block the transmission of ultraviolet light, thereby rendering such shields inoperative and requiring their quick replacement. Moreover, the use of such rigid sleeve shields may substantially reduce the life expectancy of the ultraviolet emitting fluorescent tubes by preventing sufficient heat to dissipate therefrom. This is particularly true when such shields are used to enclose "A" type fluorescent tubes since such tubes generate substantially more heat than "B" or "C" type tubes. Finally, prior art rigid tubular shields present additional drawbacks from a storage and assembly standpoint due to their multiplicity of parts, that is, the sleeve and the two end caps.

Accordingly, it is the general object of the instant invention to provide a shield for fluorescent tubes which overcomes the disadvantages of the prior art.

It is a further object of the instant invention to provide a shield for ultraviolet and emitting fluorescent tubes which exhibits a long ultraviolet light transmission expectancy.

It is a further object of the instant invention to provide a shield for use with ultraviolet emitting fluorescent tubes which freely allows tube gases and heat to dissipate into the ambient air.

It is still a further object of the instant invention to provide a shield for use with ultraviolet emitting fluorescent tubes, which is simple in construction, reusable and which exhibits a long life expectancy.

These and other objects of the instant invention are achieved by providing a protective shield for fluorescent tubes having a pair of end caps through which electrical contacts extend. The shield is formed of a flexible plastic material and comprises a sleeve having a pair of open ends, each of the ends including an opposed pair of flaps. Each of the flaps includes at least one opening therein. The sleeve is adapted to receive the tube closely therein with the flaps of each end being folded toward each other to overlap and cover an associated end cap of the fluorescent tube and with the contacts thereof extending through the openings in said overlapped flaps.

Other objects and many of the attendant advantages of this invention will become readily apparent by reference to the accompanying drawing wherein.

Figure 1:
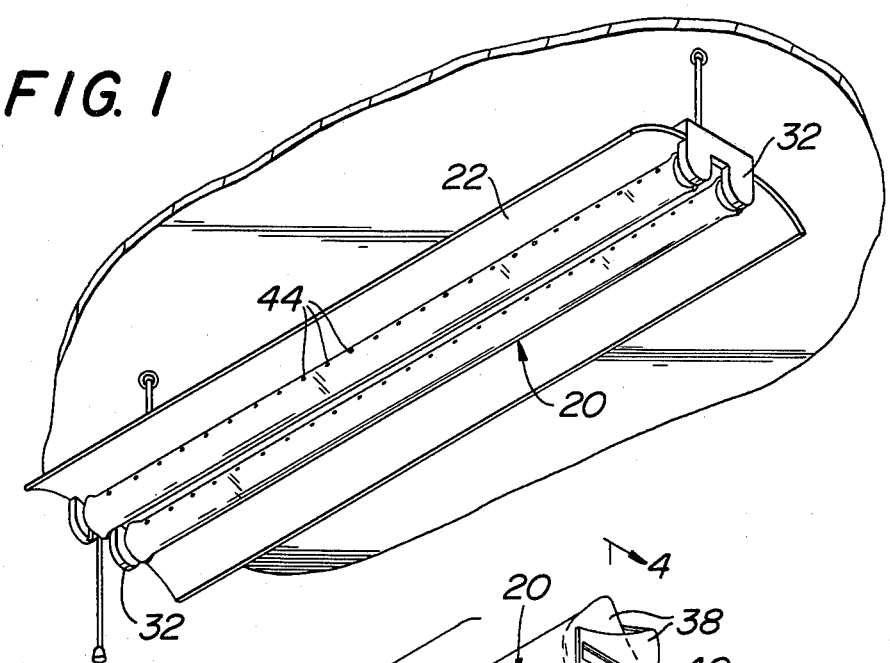
FIG. 1 is a perspective view of a conventional fluorescent fixture having a pair of fluorescent tubes each disposed within the shield of the instant invention.

Referring now in greater detail to the various figures of the drawing wherein like reference characters refer to like parts, there is in FIG. 1 a pair of protective shields 20 in accordance with the teachings of the instant invention, each enclosing a conventional fluorescent tube 24 in a lamp fixture 22. In the embodiment shown in FIG. 1, the fluorescent tubes 24 are each shown as an elongated straight tubes. That showing is merely exemplary and the tubes can be of any conventional shape, such as circles, arcs, etc.

The shield 20 of the instant invention is arranged to protect personnel in the vicinity of the tube from injury in the event that the tube should shatter. To that end, the instant invention is suitable for use in various applications making use of any type of fluorescent tube, e.g., hot cathode, cold cathode, etc., which is exposed in an uncovered fixture. In addition, owing to the particular construction of the protective shield of the instant invention, it is particularly suitable for use with ultraviolet emitting fluorescent tubes, such as used in home sunlamps, in suntanning salon booths, in poultry barns and other animal husbandry applications, in industrial solaria applications, in germicidal applications, etc.

Figure 2:
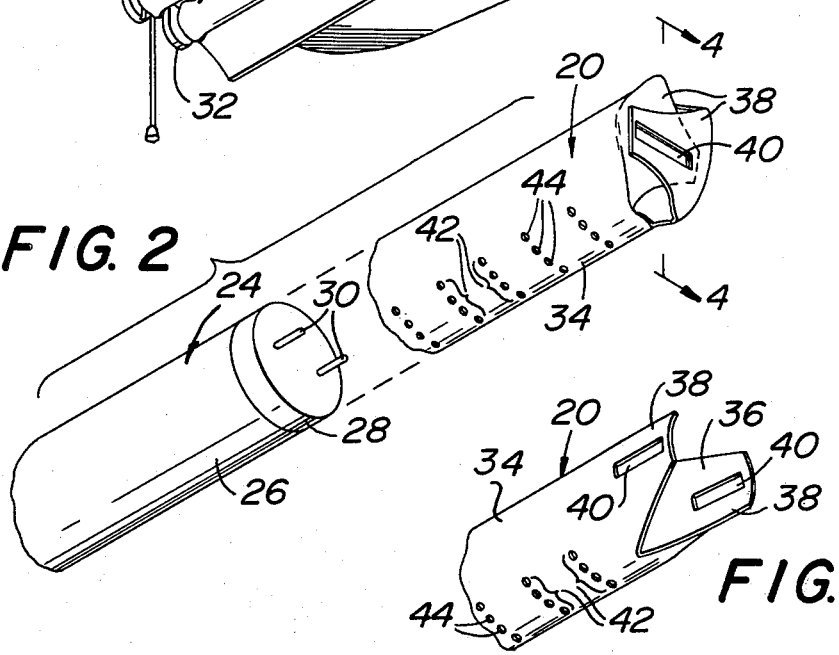
FIG. 2 is an exploded perspective view of a portion of a conventional fluorescent tube and a portion of the shield of the instant invention with its flaps folded over as in use.
Figure 3:
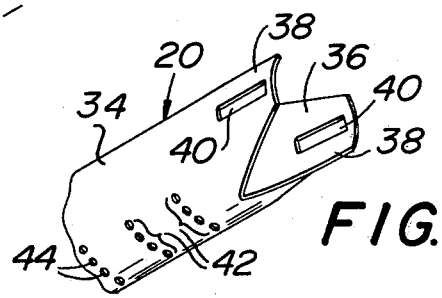
FIG. 3 is a perspective view of a portion of an empty shield of the instant invention.
Figure 4:
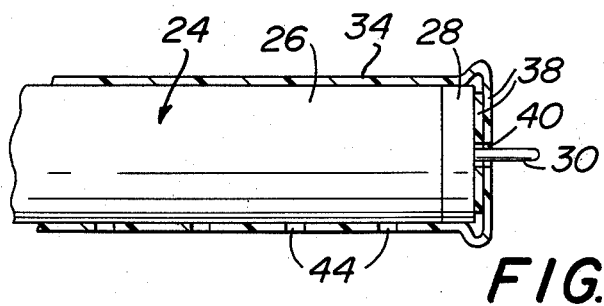
FIG. 4 is a sectional view taken along line 4—4 of FIG. 2.

To that end, as can seen in FIGS. 2, 3 and 4 the shield 20 basically comprises a sleeve of relatively thin, e.g., 10 mil (0.25 mm) flexible plastic film which exhibits high transmissivity to electromagnetic radiation in the ultraviolet spectrum. The material forming the sleeve 20 of the instant invention also exhibits resistance to degradation, discoloring and aging while being strong, tough, yet readily perforatable. One particularly suitable plastic comprises a polytethrafluroethylene fluorocarbon which does not include a ultraviolet inhibitor, such as sold by E. I. Dupont de Nemours of Wilmington, Del., under the trademark TEFLON 160 FILM. Such material exhibits high transmissivity of electromagnetic radiation of a wave length from 250 to 500 nanometers and exhibits an extremely long life before losing transmissivity or discoloring. For example, such material may exhibit up to 15,000 hours of life when used with "A"

and "B" type ultraviolet emitting fluorescent tubes and up to 4,000 hours for "C" type tubes.

The fluorescent tube 24, being of conventional construction, comprises a cylindrical glass envelope 26 sealed at either end by a respective electrically insulative cap 28. A pair of prongs or electrical contacts 30 project normally from each end cap for electrical connection to the fixture receptacles 32.

The shield 20 basically comprises a sleeve, 34 formed of said flexible film, which is adapted to receive the fluorescent tube 24 snuggly therein. To that end, the inside diameter of the sleeve is just slightly greater than the outside diameter of the tube. The sleeve is open at each end 36. Each end 36 is in the form of a pair of opposed triangular flaps or tabs 38 which are disposed diametrically to each other. An elongated slot 40 is located in each tab, with the longitudinal axis of the slot being parallel to the longitudinal axis of the sleeve. The distance between the flaps at one end of the sleeve and the flaps at the other end of the sleeve, defines the body of the shield and is equal to the length of the fluorescent tube 24. A plurality of lines 42 of plural openings or air vents 44 is provided in the body of the sleeve, that is, between the opposed ends 36 along the entire length of the sleeve. Each line extends for approximately one quarter of the transverse periphery of the sleeve and is centered along the semicircular arc of the transverse periphery extending between the slots 40. Each line is spaced from the adjacent line along the longitudinal axis of the sleeve by approximately 1 inch (25.4 mm), with the spacing between the vents 44 in each line being approximately equal to 0.25 inch (6.25 mm). The diameter of each of the vents 38 is approximately 0.125 inch (3.12 mm).

The tube 24 is located within the shield as follows: The tube is slid into the shield so that its body portion is centered therein. One flap 38 at one end 36 is then folded over the end cap 28 of the tube so that the prongs 30 extend through to the slot 40 in the flap. The other flap at that end is then folded over the first folded flap so that the prongs 30 also extend though the slot 40 in that flap. The two flaps at the opposite end of the shield 20 are folded over the prongs at the other end of the tube 24 in the same manner.

Once the tube 24 is located within the shield 20, with the flaps folded over as described above, the tube is ready for mounting in an exposed tube fixture 22.

The plastic material forming the shield serves to strengthen the glass envelope of the tube, thereby providing a safeguard against tube breakage due to impact. In the event that the tube is impacted sufficiently hard to cause it to shatter, the shield retains the shards of glass therein.

When the tubes with the shields 20 thereon are in place in the fixture. The vents 38 are disposed closest to the fixture, i.e., directed upward. This feature ensures that heat and gases readily escape from the sleeve to allow tube gases and heat to be dissipated into the ambient atmosphere. The dissipation of heat from fluorescent tubes is of considerable importance, particularly for "A" and "B" type tubes, which tubes generate substantially more heat than "C" type tubes. It must be pointed out at this juncture, in applications having fluorescent tubes which do not generate substantial heat, the shield need not include any air vents 38 or may include a lesser number than shown and described heretofore.

As will be appreciated from the foregoing, the protective shield of the instant invention is simple in construction, can be readily stored in a "lay flat" condition when not in use and does not require substantial assembly to enclose a conventional fluorescent tube. With the tube in place within the shield, the tube is protected against breakage due to impact and, if such breakage should occur, the shield serves to retain the shattered glass shards within the shield, thereby protecting persons in the vicinity of the lamp. The material forming the shield allows erythemal ultraviolet radiation to be transmitted to the ambient surroundings with very little degradation and over a long period of time. The perforations allow the slow release of tube gas into the air while also serving to dissipate substantial heat from the tube, thereby increasing tube life. Moreover, the shield of the instant invention can be readily reused by merely withdrawing the fluorescent tube from within the shield and placing a replacement tube therein.

Without further elaboration, the foregoing will so fully illustrate my invention that others may, by applying current or future knowledge, readily adapt the same for use under various conditions of service.

What is claimed as the invention is:

1. A protective shield for a fluorescent tube having a pair of end caps through which at least one electrical contact extends, said shield being formed of a flexible plastic material and comprising a sleeve having a pair of open ends, each of said ends including an opposed pair of lamps, each of said flaps including at least one opening therein, said sleeve being adapted to receive said tube closely therein with the flaps of each end being folded over each other to overlap and cover an associated end cap of said tube and with said contacts extending through the openings in said flaps.

2. The shield of claim 1 wherein said plastic material is transmissive to electromagnetic radiation in the ultraviolet spectrum.

3. The shield of claim 1 wherein said sleeve includes plural air vents therein.

4. The shield of claim 3 wherein said plastic material comprises a polytetrafluroethylene fluorocarbon film not having an ultraviolet inhibitor.

5. The shield of claim 4 wherein said film is approximately 10 mils (0.25 mm) thick.

6. The shield of claim 3 wherein said air vents are confined to a predetermined portion of the periphery of said sleeve.

7. The shield of claim 6 wherein said vents are confined to less than one half of the periphery of said shield.

8. The shield of claim 7 wherein said air vents are disposed in plural lines, each line being spaced from an immediately adjacent line by approximately 1 inch (25.4 mm), wherein the vents in each line are spaced by approximately ¼ inch (6.4 mm) and wherein the diameter of each vent is approximately ⅛ inch (3.125 mm).

9. The shield of claim 8 wherein each of said flaps are of generally triangular shape.

10. The shield of claim 9 wherein the openings in each of said flaps comprise a longitudinally extending elongated slot.

* * * * *